United States Patent [19]
Yamada et al.

[11] Patent Number: 5,512,170
[45] Date of Patent: Apr. 30, 1996

[54] LIQUID CHROMATOGRAPH

[75] Inventors: Yoshiaki Yamada, Ishioka; Hironori Kaji, Hitachinaka, both of Japan

[73] Assignee: Hitachi, Ltd., Tokyo, Japan

[21] Appl. No.: 356,751

[22] Filed: Dec. 15, 1994

[30] Foreign Application Priority Data

Dec. 27, 1993 [JP] Japan ................... 5-330597

[51] Int. Cl.$^6$ ................................. B01D 15/08
[52] U.S. Cl. ..................... 210/198.2; 210/656
[58] Field of Search ................... 210/656, 659, 210/198.2; 96/102; 422/70

[56] References Cited

U.S. PATENT DOCUMENTS

| | | | |
|---|---|---|---|
| 5,089,124 | 2/1992 | Mahar | 210/198.2 |
| 5,091,092 | 2/1992 | Newhouse | 210/198.2 |
| 5,100,557 | 3/1992 | Nogami | 210/198.2 |
| 5,107,908 | 4/1992 | Newhouse | 210/198.2 |
| 5,180,487 | 1/1993 | Saito | 210/198.2 |
| 5,234,587 | 8/1993 | Allington | 210/198.2 |
| 5,294,336 | 3/1994 | Mizuno | 210/198.2 |

Primary Examiner—Ernest G. Therkorn
Attorney, Agent, or Firm—Kenyon & Kenyon

[57] ABSTRACT

The volume of the sample added to the sample retainer and the capacity of the sample retainer are compared, and the less one is stored as volume of the sample injected to a sample separating column. If the volume of the sample added to the sample retainer is more than the capacity of the sample retainer, accordingly, the capacity of the sample retainer is stored.

18 Claims, 13 Drawing Sheets

FIG. 9

FOR ADDED VOLUME OF 10 μℓ
ANALYSIS DATE AND TIME: JULY 26, 1992; 20:00
FILE NAME:                          CALIBRATION METHOD: EXTERNAL STANDARD
SAMPLE NAME: STANDARD SAMPLE 1      VIAL NO.: 1    INJECTED
VOLUME: 10 μℓ

FOR ADDED VOLUME OF 20 μℓ
ANALYSIS DATE AND TIME: JULY 26, 1992; 20:20
FILE NAME:                          CALIBRATION METHOD: EXTERNAL STANDARD
SAMPLE NAME: STANDARD SAMPLE 1      VIAL NO.: 1    INJECTED
VOLUME: 20 μℓ

FOR ADDED VOLUME OF 50 μℓ
ANALYSIS DATE AND TIME: JULY 26, 1992; 20:40
FILE NAME:                          CALIBRATION METHOD: EXTERNAL STANDARD
SAMPLE NAME: STANDARD SAMPLE 1      VIAL NO.: 1    INJECTED
VOLUME: 50 μℓ ?

FOR ADDED VOLUME OF 100 μℓ
ANALYSIS DATE AND TIME: JULY 26, 1992; 21:00
FILE NAME:                          CALIBRATION METHOD: EXTERNAL STANDARD
SAMPLE NAME: STANDARD SAMPLE 1      VIAL NO.: 1    INJECTED
VOLUME: 100 μℓ ?

FOR ADDED VOLUME OF 200 μℓ
ANALYSIS DATE AND TIME: JULY 26, 1992; 21:20
FILE NAME:                          CALIBRATION METHOD: EXTERNAL STANDARD
SAMPLE NAME: STANDARD SAMPLE 1      VIAL NO.: 1    INJECTED
VOLUME: 100 μℓ ?

FOR ADDED VOLUME OF 500 μℓ
ANALYSIS DATE AND TIME: JULY 26, 1992; 21:40
FILE NAME:                          CALIBRATION METHOD: EXTERNAL STANDARD
SAMPLE NAME: STANDARD SAMPLE 1      VIAL NO.: 1    INJECTED
VOLUME: 100 μℓ

FOR ADDED VOLUME OF 1000 μℓ
ANALYSIS DATE AND TIME: JULY 26, 1992; 22:00
FILE NAME:                          CALIBRATION METHOD: EXTERNAL STANDARD
SAMPLE NAME: STANDARD SAMPLE 1      VIAL NO.: 1    INJECTED
VOLUME: 100 μℓ

FIG. 11

THE EXAMPLE OF REPORT, WHEN 20 μℓ SAMPLE IS LOADED
(SAMPLE LOOP VOL: 100 μℓ)

```
                    ANALYSIS RESULT REPORT

ANALYSIS      : 08/26/92  20:00      REPORT        : 08/26/92  20:15
METHOD FILE   : PAH                  CALIB METHOD  : EXT STD
DATA FILE     : PAH001                SAMPLE NAME   : UNK001
VIAL NO.      : 1                    INJECTION VOL : 20 μℓ
```

| PEAK NO. | RT (min) | NAME | AREA (μℓ·sec) | CONC (ppm) |
|---|---|---|---|---|
| 1 | 2.02 | BENZENE | 300528 | 0.200 |
| 2 | 2.44 | NAPHTALENE | 66132 | 3.200 |
| 3 | 4.45 | ANTHRACENE | 305925 | 3.300 |

FIG. 12

THE EXAMPLE OF REPORT, WHEN 100 μℓ SAMPLE IS LOADED
(SAMPLE LOOP VOL: 100 μℓ)

```
               ANALYSIS RESULT REPORT
ANALYSIS      : 08/26/92  20:20    REPORT        : 08/26/92  20:35
METHOD FILE   : PAH                CALIB METHOD  : EXT STD
DATA FILE     : PAH001             SAMPLE NAME   : UNK002
VIAL NO.      : 2                  INJECTION VOL : 100 μℓ
```

| PEAK NO. | RT (min) | NAME | AREA (μℓ·sec) | CONC (ppm) |
|---|---|---|---|---|
| 1 | 2.01 | BENZENE | 1202110 | 0.799 |
| 2 | 2.43 | NAPHTALENE | 264530 | 12.801 |
| 3 | 4.46 | ANTHRACENE | 1223700 | 13.200 |

FIG. 13

THE EXAMPLE OF REPORT, WHEN 500 µℓ SAMPLE IS LOADED
(SAMPLE LOOP VOL: 100 µℓ)

```
              ANALYSIS RESULT REPORT

ANALYSIS      : 08/26/92  20:40    REPORT        : 08/26/92  20:55
METHOD FILE   : PAH                CALIB METHOD  : EXT STD
DATA FILE     : PAH001             SAMPLE NAME   : UNK003
VIAL NO.      : 3                  INJECTION VOL : 100 µℓ

PEAK NO.    RT        NAME              AREA          CONC
          (min)                       (µℓ·sec)        (ppm)
─────────────────────────────────────────────────────────────
   1       2.01    BENZENE            1502640         1.000
   2       2.45    NAPHTALENE          330665        16.001
   3       4.43    ANTHRACENE         1529620        16.498
─────────────────────────────────────────────────────────────
```

LIQUID CHROMATOGRAPH

BACKGROUND OF THE INVENTION

The present invention relates to a liquid chromatograph. More particularly, it concerns a liquid chromatograph that makes it possible to know of accurate volume of sample added to a column.

For the prior liquid chromatograph, volume of sample injected to the column is an important parameter for investigating and analyzing the chromatogram data obtained. If the chromatogram data are preserved, it is desirable to also store the volume of the sample injected to the sample separating column. So, it is usual to preserve the volume of the sample added to the sample retainer frequently called the sample loop as the volume of the sample injected to the sample separating column together with the obtained chromatogram data if there is an automatic sample injecting device for measuring the volume of the sample injected to the sample separating column with use of a syringe and the like. Or, the sample retainer capacity should be preserved as the volume of the sample injected to the sample separating column together with the obtained chromatogram data if there is an automatic sample injecting device for measuring the volume of the sample injected to the sample separating column with use of the sample retainer.

However, the use of the sample retainer described above has the disadvantage that if the volume of the sample added to the sample retainer exceeds over the capacity of the sample retainer, the volume of the sample added to the sample retainer is stored as the volume of the sample injected to the sample separating column in spite of the same volume of the sample injected to the sample separating column as the capacity of the sample retainer. This is due to no account of the fact that the volume of the sample injected to the sample separating column is determined in terms of both the volume of the sample added to the sample retainer and the capacity of the capacity of the sample retainer. Also, the sample retainer has the disadvantage that even if the volume of the sample added to the sample retainer is less than the capacity of the sample retainer, the volume of the sample added to the sample retainer may not be equal to the volume of the sample added from the sample retainer to the sample separating column. This is due to the fact that as the sample is diffused with the eluate in the piping connected with the sample retainer or in the sample retainer, all the added sample cannot be always remained in the sample retainer.

SUMMARY OF THE INVENTION

In view of solving the foregoing problems of the prior art, it is an object of the present invention to provide a liquid chromatograph that can refer to the capacity of the sample retainer as the volume of the sample injected to the sample separating column if the volume of the sample added to the sample retainer exceeds over the capacity of the sample retainer.

Another object of the present invention is to provide a liquid chromatograph that makes it possible to easily determine the situation of the sample fed to the sample separating column even if the volume of the sample added to the sample retainer is less than the capacity of the sample retainer.

Briefly, the foregoing objects are accomplished in accordance with aspects of the present invention by the liquid chromatograph that comprises a sample separating column, means for making an eluate to flow through the sample separating column, a sample retainer having a predetermined capacity, means for adding a sample to the sample retainer before injecting the added sample to the sample separating column to separate, means for detecting the sample separated by the sample separating column, and means for comparing or storing volume of the sample added to the sample retainer and the capacity of the sample retainer.

The liquid chromatograph of the present invention has the advantage that if the volume of the sample added to the sample retainer is compared with the capacity of the sample retainer, determination can be made as to which of the two is more or less than the other. If the volume of the sample added to the sample retainer is more than the capacity of the sample retainer, therefore, one can determine that the capacity of the sample retainer is the volume of the sample injected to the sample separating column. In other words, the liquid chromatograph according to the present invention can refer to the capacity of the sample retainer as the volume of the sample injected to the sample separating column if the volume of the sample added to the sample retainer is more than the capacity of the sample retainer. In the case that both the volume of the sample added to the sample retainer and the capacity of the sample retainer are stored, the stored data can be used to determine which of the two is more or less, because of the storing. This can accomplish the objects of the present invention accordingly. Even if the volume of the sample added to the sample retainer is less than the capacity of the sample retainer, the liquid chromatograph of the present invention can identify such a volume of the sample that no difficulty is caused by the diffusion phenomenon effected between the sample and eluate, or the volume of the sample that is less quantity by which the sample cannot be discharged together with the eluate even if the sample and eluate diffuse. An operator therefore can know that more volume of the sample injected to the sample separating column than the specific volume of the sample becomes unstable.

BRIEF DESCRIPTION OF THE DRAWINGS

FIG. 9 is a list illustrating headers of a calculation report data obtained as results of an analysis according to the present invention;

FIG. 11 is a list illustrating a first analysis result report;

FIG. 12 is a list illustrating a second analysis result report;

FIG. 13 is a list illustrating a third analysis result report; and

DESCRIPTION OF THE PREFERRED EMBODIMENTS

Figure 2:
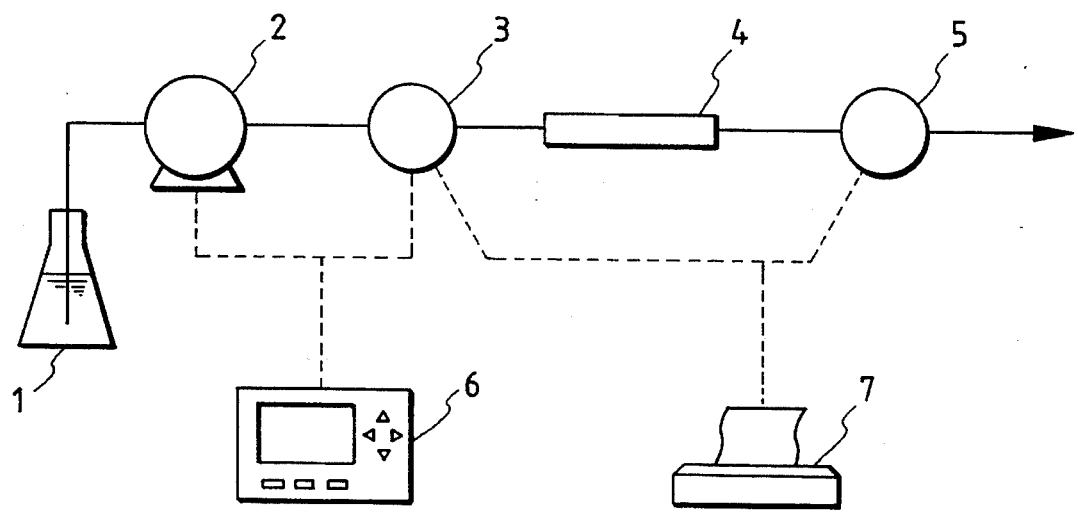
FIG. 2 is a block diagram illustrating principles of an embodiment of the liquid chromatograph according to the present invention.

FIG. 2 depicts a block diagram illustrating an embodiment of the liquid chromatograph according to the present invention. An eluate in an eluate reservoir 1 is made to flow through a sample separating column 4 by a pump 2. A sample is injected into the sample separating column 4 by a sample injecting device 3. The sample is separated into components according to differences of affinity of the sample from a loading material filled in the sample separating column 4. The separated components are detected by a detector 5. A controller 6 makes a concentration control of conditions for a flow rate by the pump 2 and for volume of the sample injected to the sample separating column 4 by the sample injecting device 3. A data processing device 7 records and stores changes of signals fed out of the detector 5 and calculates contents of the eluate components in terms of eluate areas and heights of peaks of the eluate components. To maintain a reliability of the obtained calculation data, the data processing device 7 records and stores the volume of the sample injected to the sample separating column 4 by the sample injecting device 3 together with the data.

Figure 3:
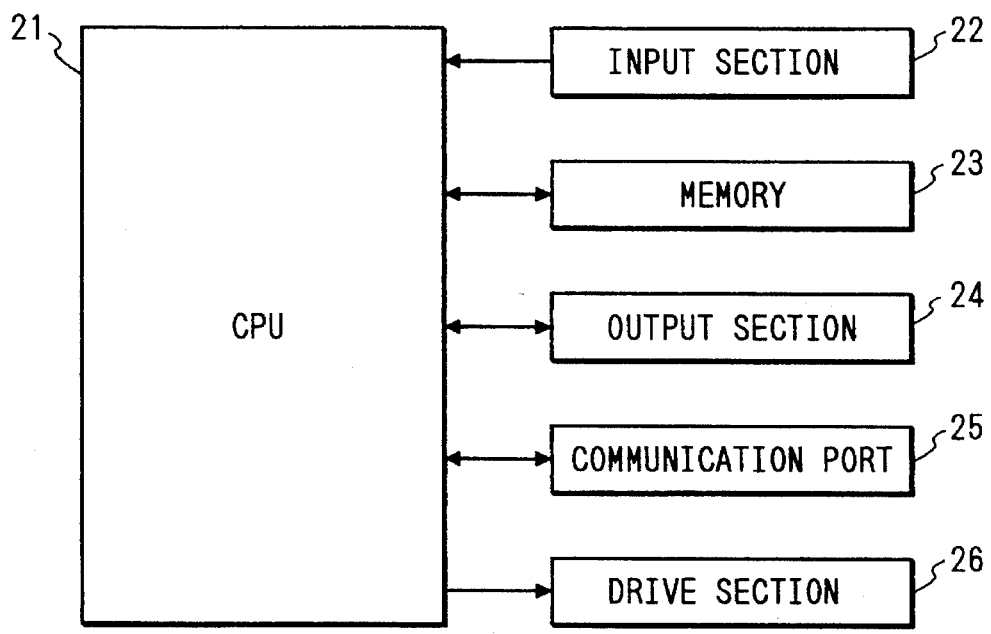
FIG. 3 is a block diagram illustrating an embodiment of configuration of the controller for the sample injecting device shown in FIG. 2.

FIG. 3 depicts a block diagram illustrating an example of configuration of the controller 6 for the sample injecting device 3. The controller 6 comprises a central processing unit (CPU) 21, an input section 22, such as a keyboard, for entering the conditions, such as capacity of a sample retainer and the volume of the added sample, a memory 23 for storing them, an output section (LCD) 24 for supporting for entering the conditions and making it possible to check them, communication port 25 for sending the conditions stored in the memory 23 to other units, and a drive 26 for driving a motor for a valve, which will be described later. The controller 6 can be connected with an output unit (not shown) for injecting out the volume of the added sample, the capacity of the sample retainer, measurement conditions, and measurement results.

Figure 5:
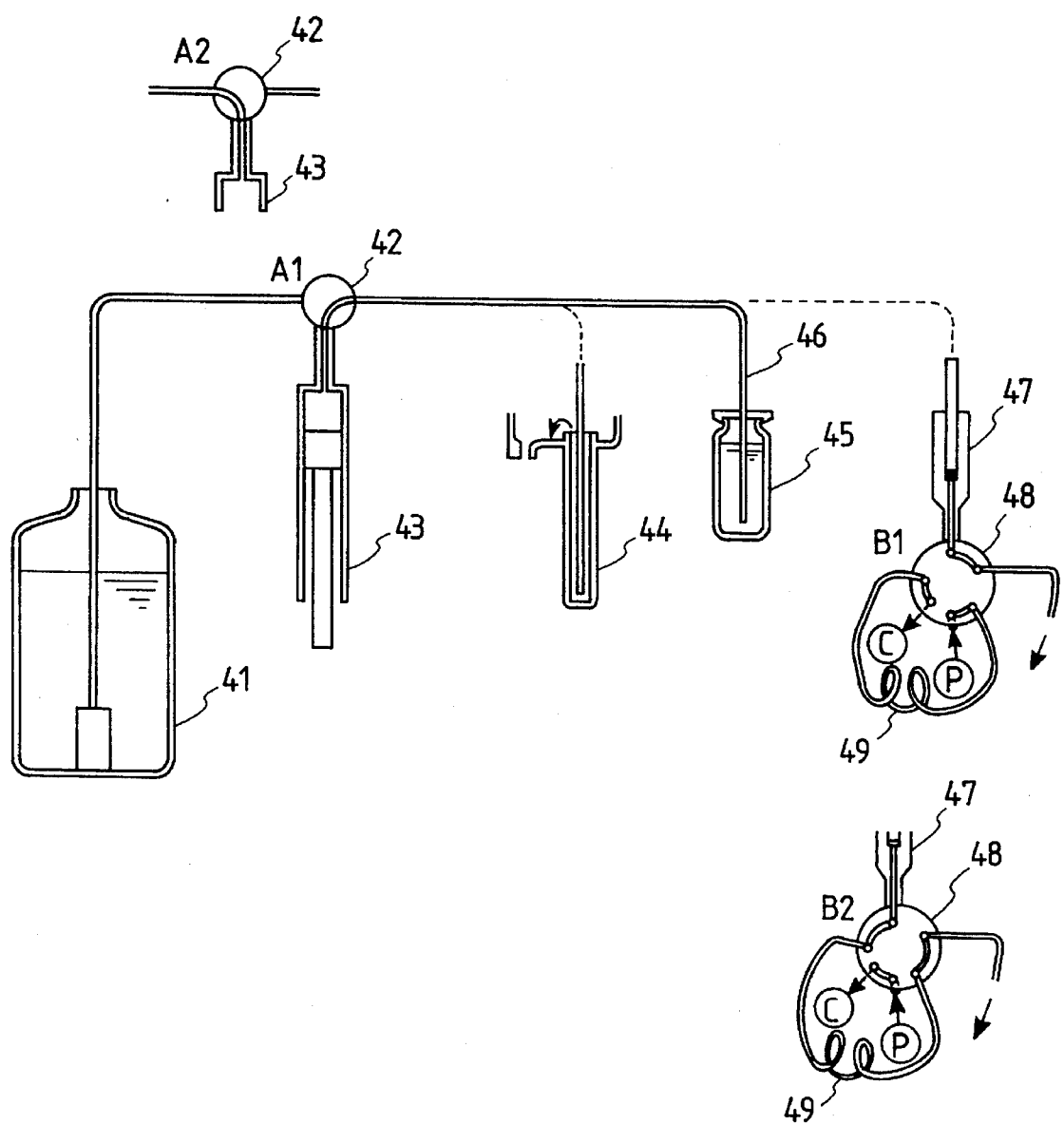
FIG. 5 is a sketch illustrating a flow route of the sample injecting device shown in FIG. 2.

FIG. 5 depicts a sketch illustrating a flow route of the sample injecting device 3 of the present invention. If a valve 42 is set at a position indicated by A1, the sample in sample container 45 is sucked out through a needle 46 by a syringe 43. After this, the needle 46 is replaced to an injection port 47. Then, an injection valve 48 is switched at a position indicated by B2 before the syringe 43 sucks out the sample. The sample is injected to a sample retainer 49 ordinarily called a sample loop. Finally, the injection valve 48 is switched to a position indicated by B1. The sample is injected through an analyzing flow route to the sample separating column 4. A cleaning port 44 has a cleaning liquid sucked from a cleaning liquid container 41 by way of the syringe 43, with the valve 42 switched to a position indicated by A2. The cleaning liquid is discharged into the cleaning port 44 by way of the syringe 43 to clean the flow route including the needle 46, with the valve 42 switched to the position indicated by A1. Encircled C and P in the figure denote the pump 2 and the sample separating column 4, respectively.

Figure 6:
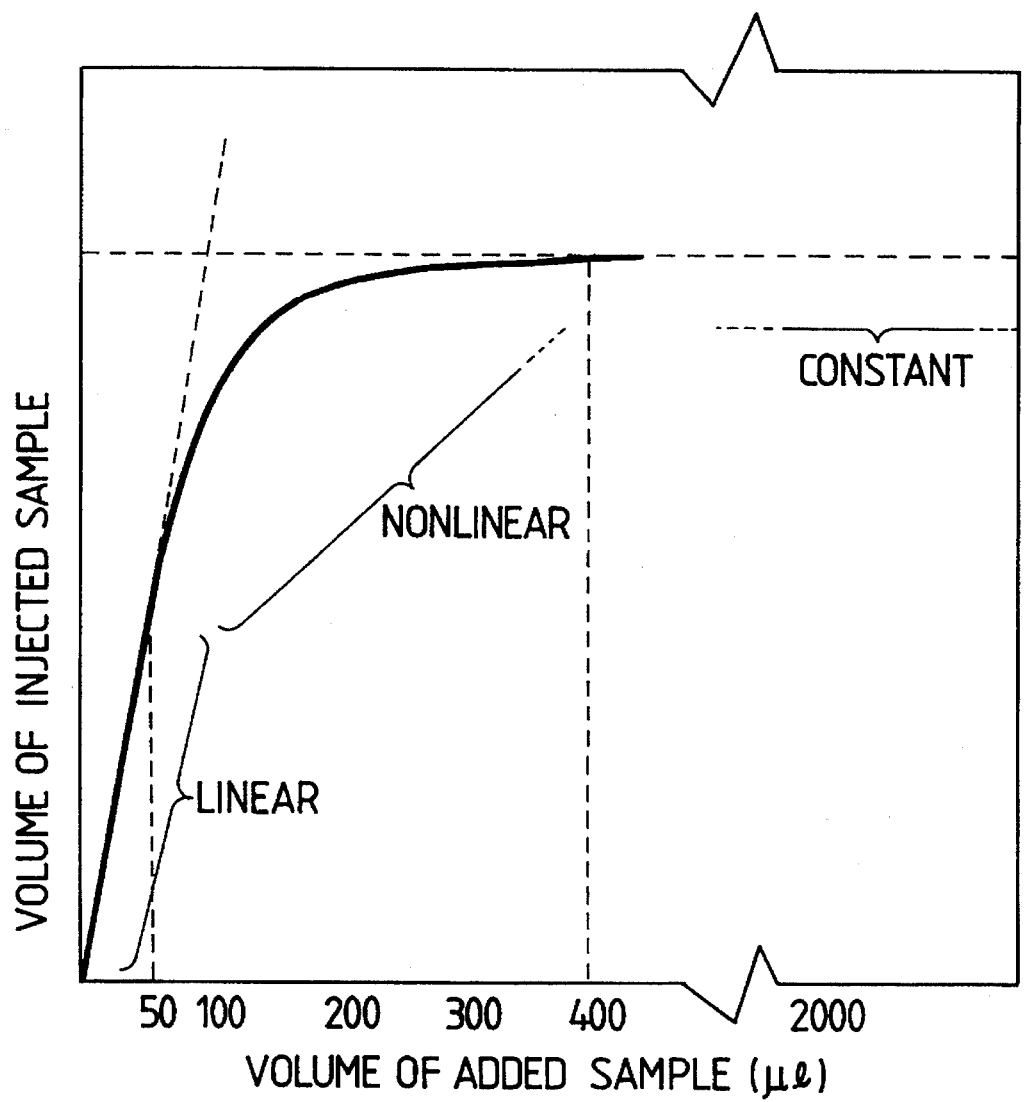
FIG. 6 is a graph illustrating a curve of the volume of sample injected in the sample separating column with respect to the volume of sample added in the sample retainer, with the sample retainer shown in FIG. 5 having the capacity of 100 ml as an example.

FIG. 6 depicts a graph illustrating a curve of the volume of sample (peak area) injected in the sample separating column 4 with respect to the volume of sample added in the sample retainer 49, with the sample retainer 49 having the capacity of 100 ml as an example. If the volume of sample added in the sample retainer 49 is not more than 50% of the capacity of the sample retainer, the curve is linear. In the linear range, the volume of injected sample is determined in terms of the volume of added sample. If the volume of sample added in the sample retainer 49 is more than 400% of the capacity of the sample retainer, the volume of injected sample is determined constant to the capacity of the sample retainer irrespective of the volume of added sample. The volume of 400% is a value when the sample is exactly injected to the sample separating column 4. If the real volume of sample of 200% of the capacity of the sample retainer 49 is injected to the sample retainer 49, the sample virtually equal to the capacity of the sample retainer 49 can be injected to the sample separating column 4. If the volume of sample added to the sample retainer 49 is 50 to 400% of the capacity of the sample retainer 49, however, the volume of sample injected into the sample separating column 4 is in a nonlinear relationship with the volume of sample added to the sample retainer 49. The volume of sample injected to the sample retainer 49 does not come beyond and is not determined by either of the volume of sample added to the sample retainer 49 or the capacity of the sample retainer 49.

Figure 1:
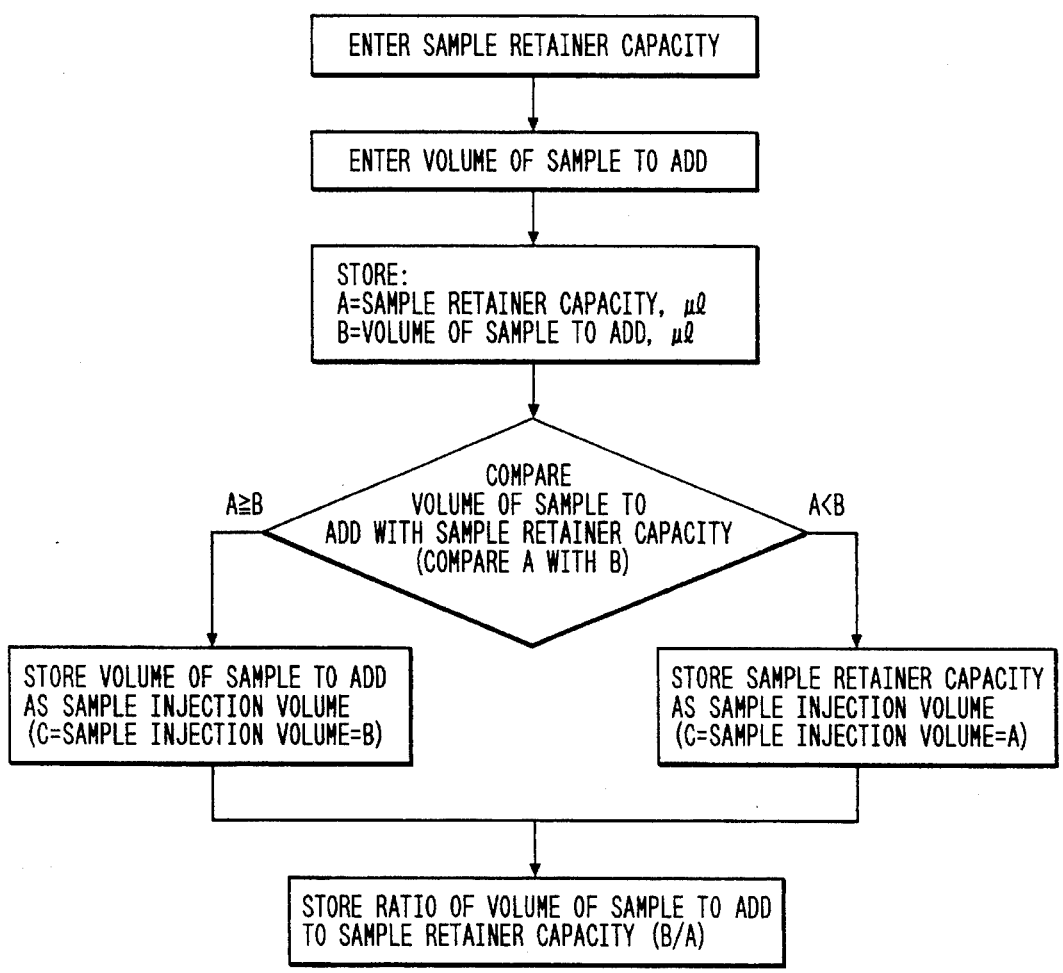
FIG. 1 is an example of algorithm according to the present invention illustrating storing the volume of sample injected into the sample separating column.

FIG. 1 depicts an algorithm illustrating storing the volume of sample injected into the sample separating column 4. The algorithm is for fetching the volume B of sample added to the sample retainer 49 and the capacity A of the sample retainer 49 to store. Fetching may be preceded by either of them. The stored capacity A and volume B are compared with each other. The less volume of the two is stored as the volume of sample injected to the sample separating column 4. That is, if the volume of sample added to the sample retainer 49 is less than the capacity of the sample retainer 49, the capacity of the sample retainer 49 is stored as volume C of sample injected to the sample separating column 4. If the volume of sample added to the sample retainer 49 is not less than that, on the other hand, the capacity of the sample retainer 49 is stored as the volume C. At the same time, a ratio, or a difference, of the volume of sample added to the sample retainer 49 to the capacity of the sample retainer 49 is stored.

With the algorithm, one can see whether the volume of sample injected to the sample separating column 4 represents the volume of sample added to the sample retainer 49 or the one determined by the capacity of the sample retainer 49. In other words, the volume of sample injected to the sample separating column 4 can be identified to store right.

The data comparison can be made either in the sample injecting device 3 or in a data process step after both the volume of sample added to the sample retainer 49 and the capacity of the sample retainer 49 are stored in the data processing device 7.

In FIG. 1, A≧B and A<B can be replaced by A>B and A≧B, respectively.

Figure 7:
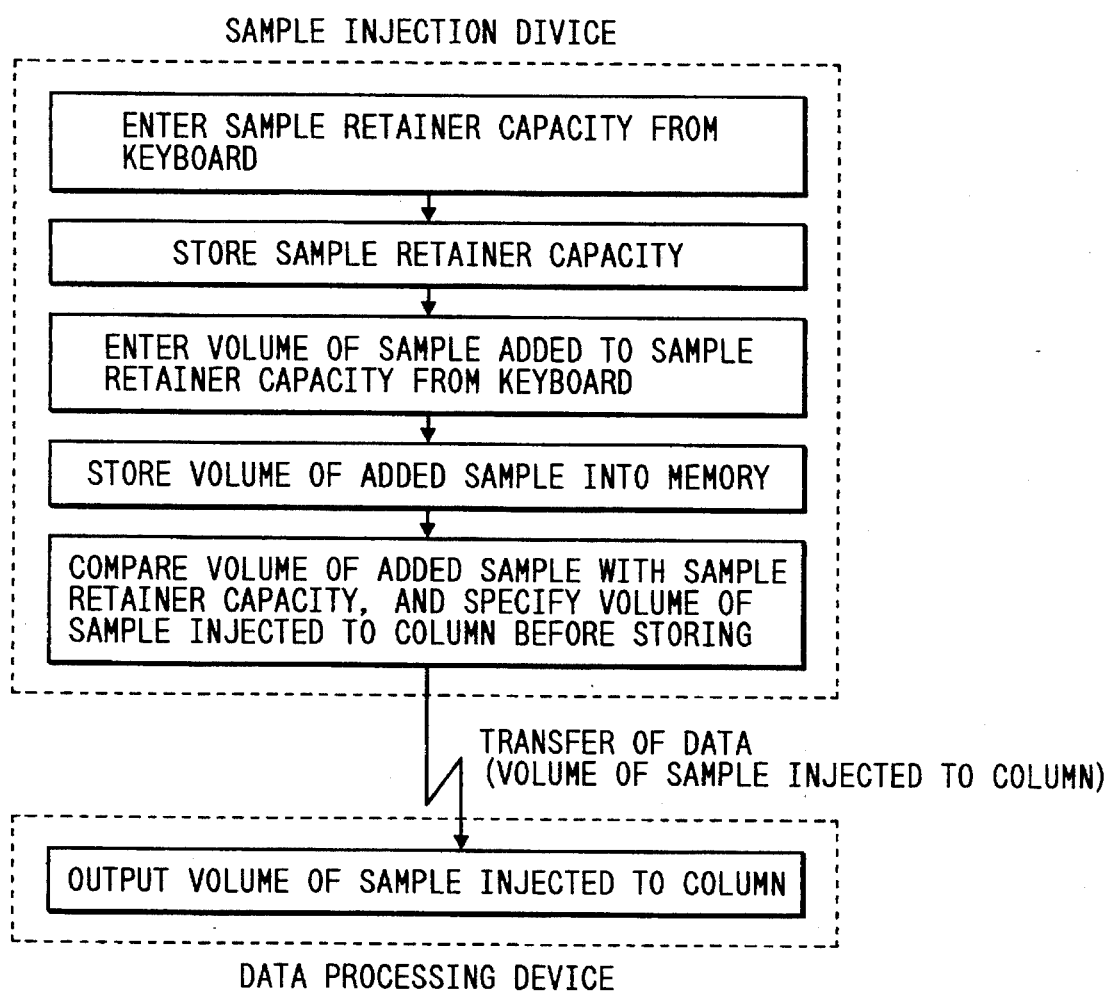
FIG. 7 is an example of algorithm according to the present invention illustrating the comparison of the capacity of the sample retainer with the volume of sample added to the sample retainer by means of the sample injecting device shown in FIG. 1.
Figure 8:
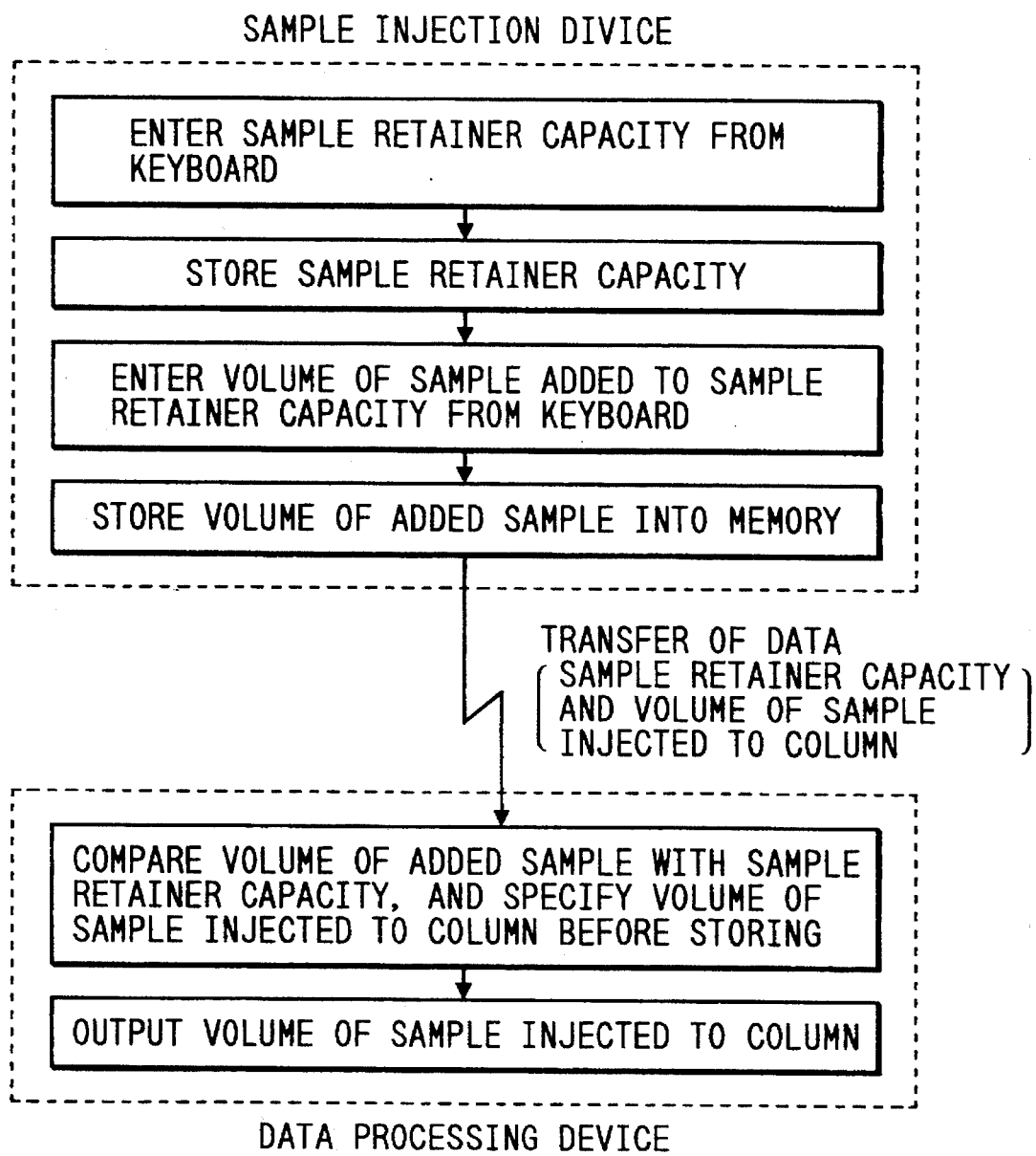
FIG. 8 is an example of algorithm illustrating the comparison of the capacity of the sample retainer with the volume of sample added to the sample retainer by means of the data processing device shown in FIG. 1.

FIG. 7 depicts an algorithm illustrating the comparison of the capacity of the sample retainer 49 with the volume of sample added to the sample retainer 49 by means of the sample injecting device 3. FIG. 8 depicts an algorithm illustrating the comparison made by means of the data processing device 7. In FIG. 7, the sample retainer capacity and the volume of sample added to the sample retainer 49 are entered and stored before being compared with each other and on the basis of a result, the less volume is stored by the sample injecting device 3. The stored volume of sample is sent to the data processing device 7 as the one injected to the sample separating column 4 before being fed out. In FIG. 8, on the other hand, the capacity of the sample retainer 49 and the volume of sample added to the sample retainer 49 are entered and stored by the sample injecting device 3. Both the stored data are sent to the sample injecting device 3. The sample injecting device 3 compares the both data and on the basis of a result, stores and feeds out the less data.

FIG. 9 depicts a list illustrating headers of a calculation report data obtained as results of an analysis with the volume of sample added to the sample retainer 49 changed to 10, 20, 50, 100, 200, 500, and 1,000 ml by means of the sample injecting device 3 having the sample retainer capacity of 100 ml. The volume of sample injected in the sample separating column 4 entered at block "INJECTION VOL" is the one added to the sample retainer 49 if the volume of sample added to the sample retainer 49 is 10 to 100 ml. That is 100 ml of the sample retainer capacity if the volume of sample added to the sample retainer 49 is 100 to 1,000 ml. The value entered at the block "INJECTION VOL" is followed by "?" if the volume of sample added to the sample retainer 49 is 50 to 400 ml that is 50 to 400% of the sample retainer capacity. Therefore, one cannot only easily confirm the volume of sample injected to the sample separating column 4, but also confirm that the volume of sample injected to the sample separating column 4 is in the range (nonlinear range) in which it cannot be identified with respect to any of the added volume of sample or the sample retainer capacity. This can increase the reliability of data.

Figure 10:
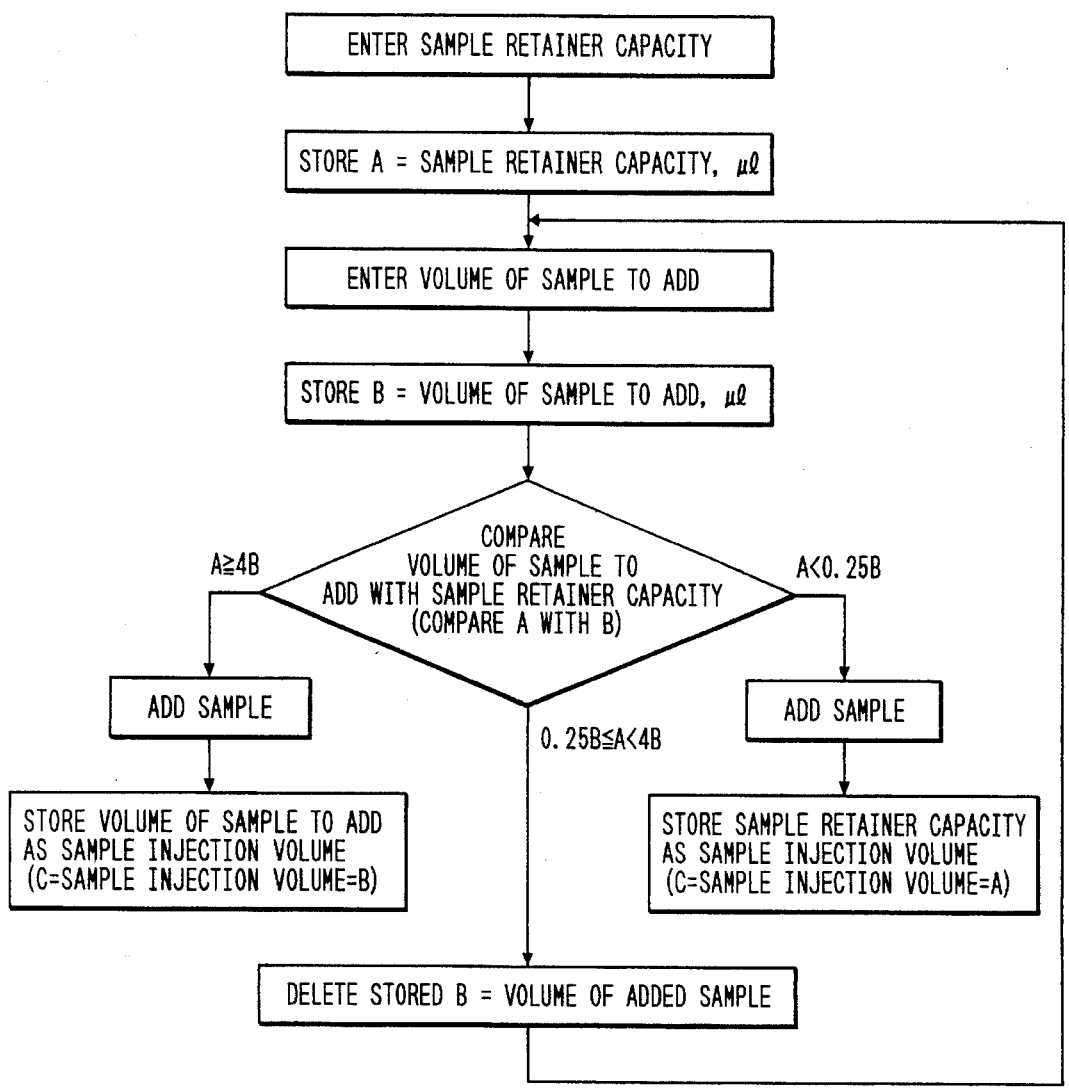
FIG. 10 is another example of algorithm according to the present invention illustrating storing the volume of sample injected to the sample separating column.

When the volume of sample injected to the sample separating column 4 is in the range (nonlinear range) in which it cannot be identified, there is another embodiment that does not allow setting the volume of sample added to the sample retainer 49, thereby increasing the reliability of data. In the embodiment, if the sample retainer capacity is 100 ml, for example, the volume of sample added to the sample retainer 49 is made not to set to 50 to 400 ml. FIG. 10 depicts an algorithm illustrating storing the volume of sample injected to the sample separating column 4. With the algorithm, the sample retainer capacity and the volume of sample added to the sample retainer 49 are entered and stored before being compared with each other. If as a result, the sample retainer capacity is four or more times or 0.25 or less times the volume of sample added to the sample retainer 49, the sample is added to the sample retainer 49. In the former case the volume of sample added to the sample retainer 49 is stored as the volume of sample injected to the sample separating column 4. In the latter case the sample retainer capacity is stored as the volume of sample injected to the sample separating column 4. In the other cases, the stored data are deleted.

In FIG. 10, A≧4B, A<0.25B, and 0.25B≦A< 4B can be replaced by A>4B, A≦0.25B, and 0.25B<A≦4B.

FIGS. 11, 12, and 13 depict lists illustrating analysis result reports of the measurement results obtained on the basis of the above-described algorithms. The reports are fed out by the data processing device 7 shown in FIG. 2. The three measurements were carried out for benzene, naphthalene, and anthracene with use of the sample injecting device 3 and the sample retainer (sample loop) 49 having the capacity of 100 ml. In the measurements, the volume of sample added to the sample retainer 49 and the volume of sample fed to the sample retainer 49 are characterized by the curve in FIG. 6.

FIG. 11 depicts the list illustrating the analysis result report when the measurement had the sample of 20 ml required therefor. The sample volume of 20 ml, as shown in FIG. 6, is an amount of sample fed to the sample retainer 49. In the embodiment, the sample volume is the amount of sample in a range where the volume of sample determined by motion of a piston of the syringe 43 is equal to the one fed into the sample separating column 4. The syringe 43 therefore should be set to feed the sample of 20 ml so that the sample separating column 4 can have the sample of 20 ml fed thereto.

FIG. 12 depicts the list illustrating the analysis result report when the measurement had the sample of 100 ml required therefor. In the measurement was output the report when the sample volume of only 100 ml was fed from the syringe 43, although FIG. 6 shows that the volume of sample of 400 ml is required to feed the sample of 100 ml to the sample separating column 4. The analysis result report has an asterisk * marked to indicate the injection volume of sample. The asterisk * denotes that the value of 100 ml is not reliable. With this, an operator can know that the measurement results also cannot be reliable to a certain degree.

FIG. 13 depicts the list illustrating the analysis result report when the measurement had the sample of 100 ml required therefor as in FIG. 12. In the measurement, however, the syringe 43 feeds the sample of 500 ml to the sample retainer 49. As the sample of more than 400 ml is fed, one can see that the sample separating column 4 also has the sample of more than 100 ml fed thereto, as shown in FIG. 6.

Figure 4:
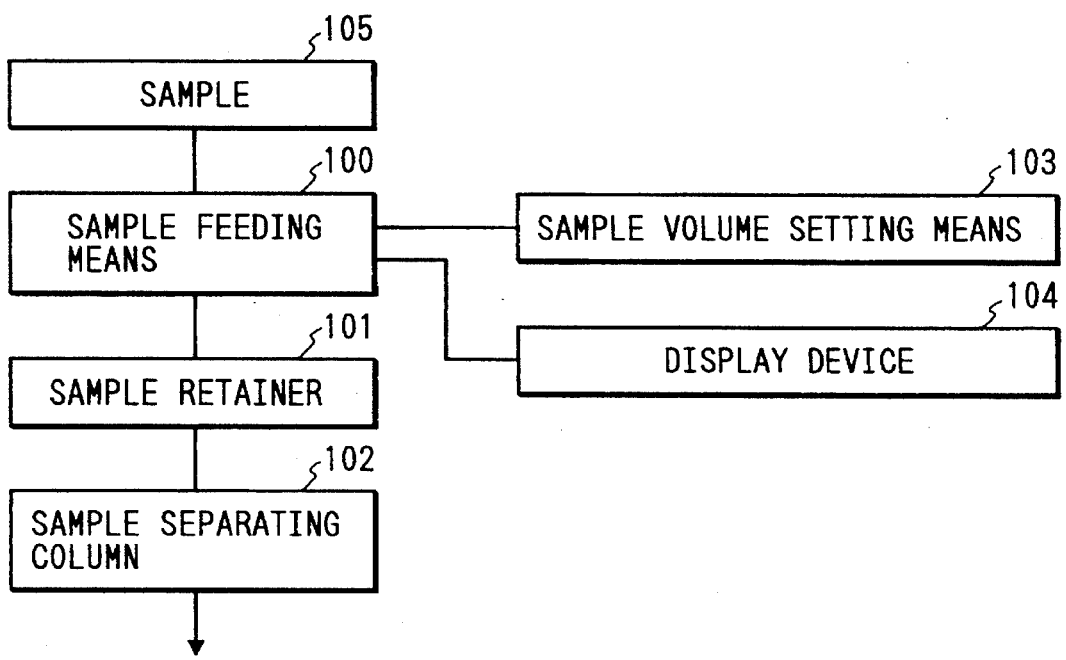
FIG. 4 is a system diagram illustrating that the sample is fed to the sample separating column.

FIG. 4 depicts a system diagram illustrating that the sample is fed to the sample separating column 4. In the system, a sample feeding means 100 has a sample volume setting means 101. The sample feeding means 100 in the embodiment of the present invention is represented by the syringe 43 shown in FIG. 5. The sample volume setting means 101 can control the motion of the piston in the syringe 43 to control the volume of sample fed to the sample retainer 49.

Figure 14:
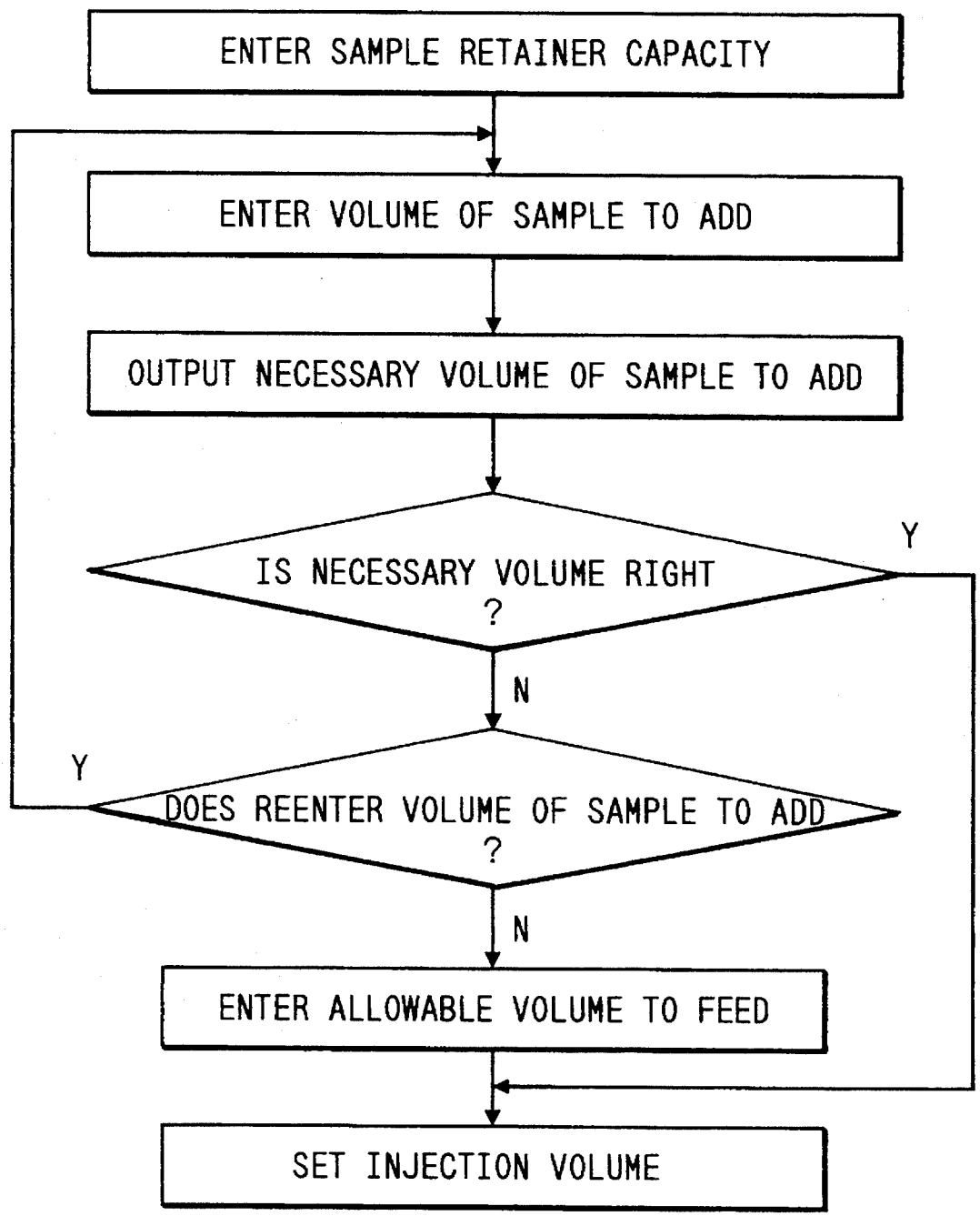
FIG. 14 is a flow diagram illustrating how to operate the system shown in FIG. 4.

FIG. 14 depicts a flow diagram illustrating how to operate the system shown in FIG. 4. First, the capacity of the sample retainer 49 is entered. The sample volume setting means 101 is used to enter the volume of sample needed for the measurement. On the basis of the entered values, the volume of sample needed to feed to the sample retainer 49 is calculated. The calculated volume is display on a display 102. The needed volume of sample is determined on the basis of the volume of sample fed to the sample retainer 49 and the volume of sample fed to the sample retainer 49 that are represented in FIG. 6. In FIG. 6, as an example, if the volume of sample to feed is 0 to 50 ml, the entered value is displayed as it is. If it is 50 ml to not more than 100 ml, it is displayed that the volume of sample to feed cannot always be fed as set, and the entered value is displayed as it is. If the volume is 100 ml, there appears a prompt that the operator should feed the sample of not less than 400 ml, as shown in FIG. 6. Also, it is displayed to request a direction of the operator whether the indicated volume should be fed or not. If so, the injection volume is set. If not, then, it is displayed to request a direction whether the volume of sample to feed would be reentered or not. The reentering step has to be made, particularly in feeding the sample of 100 ml. If the remaining sample is low or has to be saved although the operator wants to feed the sample of 400 ml, the step of entering the allowable volume of sample permits the operator to determine whether or not the measurement should be made at higher accuracy in a range of the remaining volume of sample.

The liquid chromatograph of the present invention has the advantage that if the volume of the sample added to the sample retainer exceeds over the capacity of the sample retainer, the capacity of the sample retainer can be referred to as the volume of the sample injected to the sample separating column. If the volume of the sample added to the sample retainer is less than the capacity of the sample retainer, on the other hand, the operator can recognize the range in which the sample retainer cannot accurately identify the volume of the sample. He or she can continue the operation on the basis of the recognized result. This can contribute to increasing the reliability of data.

What is claimed is:

1. A liquid chromatograph, comprising a sample retainer having a certain capacity, sample feeding means for feeding a desired volume of a sample to the sample retainer, and means for feeding the sample to a sample separating column through the sample retainer, and further comprising means for determining the lesser of volume of the sample fed from the sample feeding means and capacity of the sample retainer as volume of the sample to be injected to the sample separating column.

2. A liquid chromatograph, comprising a sample separating column, a sample retainer having a certain capacity, sample feeding means for feeding a sample to the sample retainer, and sample volume setting means for setting volume of the sample to be fed to the sample separating column, and further comprising means for setting in advance a range of volume of the sample to be fed to the sample retainer wherein when the volume of the sample set by the sample volume setting means is not more than the capacity of the sample retainer, the volume of the sample fed to the sample retainer becomes equal to the volume of the sample fed to the sample separating column, thereby identifying a value of the volume of the sample set in the range by the sample volume setting means as volume of the sample fed to the sample separating column.

3. The liquid chromatograph according to claim 2 wherein the range of the sample fed to the sample retainer is 0 to 50% of the sample retainer capacity.

4. The liquid chromatograph according to claim 3 wherein the volume of the sample needed to feed to the sample retainer is not less than 200% of the sample retainer capacity.

5. A liquid chromatograph, comprising a sample separating column, a sample retainer having a certain capacity, sample feeding means for feeding a sample to the sample retainer, which measures volume of the sample, before injecting the sample to the sample separating column, and sample volume setting means for setting volume of the sample to be fed by the sample feeding means, and further comprising means for setting in advance a range of volume of the sample to be fed to the sample retainer wherein when the volume of the sample set by the sample volume setting means is not more than the capacity of the sample retainer, the volume of the sample fed to the sample retainer becomes equal to volume of the sample fed to the sample separating column, thereby if the volume of the sample in the range is set by the sample volume setting means, identifying the set value as volume of the sample fed to the sample separating column.

6. A liquid chromatograph, comprising a sample separating column, a sample retainer having a certain capacity, sample feeding means for feeding a sample to the sample retainer, and sample volume setting means for setting volume of the sample to be fed to the sample separating column, and further comprising means for setting in advance necessary volume of the sample to be fed to the sample retainer wherein when the volume of the sample fed to the sample retainer exceeds over the capacity of the sample retainer, the capacity of the sample retainer becomes equal to the volume of the sample fed to the sample separating column, thereby if the sample not less than the necessary volume is fed to the sample retainer by the sample volume setting means, identifying the capacity of the sample retainer as the volume of the sample fed to the sample separating column.

7. A liquid chromatograph, comprising a sample separating column, a sample retainer having a certain capacity, sample feeding means for feeding a sample to the sample retainer, and sample volume setting means for setting volume of the sample to be fed to the sample separating column, wherein if volume of the sample equal to the capacity of the sample retainer is set by the sample volume setting means, volume of the sample necessary for the sample retainer is fed to the sample retainer to make the volume of the sample fed to the sample separating column equal to the capacity of the sample retainer.

8. A liquid chromatograph, comprising a sample separating column, a sample retainer having a certain capacity, sample feeding means for feeding a sample to the sample retainer, which measures volume of the sample, before injecting the sample to the sample separating column, and sample volume setting means for setting volume of the sample to be fed by the sample feeding means, and further comprising displaying means for displaying volume of the sample needed to feed to the sample retainer, wherein if volume of the sample equal to the capacity of the sample retainer is set by the sample volume setting means, the volume of the sample fed to the sample separating column is made equal to the capacity of the sample retainer.

9. A liquid chromatograph, comprising a sample retainer having a certain capacity, sample feeding means for feeding a desired volume of a sample to the sample retainer, sample volume setting means for setting volume of the sample to be fed by the sample feeding means, means for feeding the sample to a sample separating column through the sample retainer, and displaying means for displaying volume of the sample set by at least the sample volume setting means, wherein when the volume of the sample set by the sample volume setting means is not more than the capacity of the sample retainer, storing a setting range of value of volume of the sample to make volume of the sample fed to the sample retainer equal to the one fed to the sample separating column is made and when the volume of the sample set by the sample volume setting means exceeds over the capacity of the sample retainer, storing a setting range of value of volume of the sample needed to make the volume of the sample fed to the sample separating column equal to the capacity of sample retainer is made, and the displaying means makes an indication if the sample volume setting means sets the volume of sample not less or more than the setting range of value of volume of the sample.

10. A liquid chromatograph, comprising a sample retainer having a certain capacity, sample feeding means for feeding a desired volume of a sample to the sample retainer, sample volume setting means for setting volume of the sample to be fed by the sample feeding means, means for feeding the sample to a sample separating column through the sample retainer, and displaying means for displaying volume of the sample set by at least the sample volume setting means, wherein if the volume of the sample set by the sample volume setting means is equal to the capacity of the sample retainer, the displaying means indicates volume of the sample needed to feed to the sample retainer to make the volume of the sample fed to the sample separating column equal to the capacity of the sample retainer.

11. A liquid chromatograph, comprising a sample retainer having a certain capacity, sample volume setting means for setting volume of sample to be added to a sample separating column equal to the capacity of the sample retainer, and displaying means for making an indication if the volume of the sample set by the sample volume setting means is out of a range of the volume needed for highly accurate measurement of the sample retainer.

12. A liquid chromatograph, comprising a sample separating column, means for making an eluate to flow through the sample separating column, a sample retainer having a predetermined capacity, means for adding a sample to the sample retainer before injecting the added sample to the sample separating column to separate, means for detecting the sample separated by the sample separating column, and means for comparing volume of the sample added to the sample retainer with the capacity of the sample retainer, determining less one of the two, and deciding the less one as the volume of the sample injected to the sample separating column.

13. A liquid chromatograph, comprising a sample separating column, means for making an eluate to flow through the sample separating column, a sample retainer having a predetermined capacity, means for adding a sample to the sample retainer before injecting the added sample to the sample separating column to separate, means for detecting the sample separated by the sample separating column, means for comparing volume of the sample added to the sample retainer with the capacity of the sample retainer and determining less one of the two, and storing the less one as the volume of the sample injected to the sample separating column.

14. A liquid chromatograph, comprising a sample separating column, means for making an eluate to flow through the sample separating column, a sample retainer having a predetermined capacity, means for adding a sample to the sample retainer before injecting the added sample to the sample separating column to separate, means for detecting the sample separated by the sample separating column, and means for obtaining difference of volume of the sample added to the sample retainer from the capacity of the sample retainer and determining whether or not the difference is within a predetermined range.

15. The liquid chromatograph according to claim 14, further comprising means for displaying to distinguish whether the difference is within or out of the predetermined range.

16. A liquid chromatograph, comprising a sample separating column, means for making an eluate to flow through the sample separating column, a sample retainer having a predetermined capacity, means for adding a sample to the sample retainer before injecting the added sample to the sample separating column to separate, means for detecting the sample separated by the sample separating column, and means for comparing volume of the sample added to the sample retainer with the capacity of the sample retainer, determining less one of the two, obtaining difference of the volume of the sample added to the sample retainer from the capacity of the sample retainer, and determining whether or not the difference is within a predetermined range.

17. A liquid chromatograph, comprising a sample separating column, means for making an eluate to flow through the sample separating column, a sample retainer having a predetermined capacity, means for adding a sample to the sample retainer before injecting the added sample to the sample separating column to separate, means for detecting the sample separated by the sample separating column, and means for storing less one of volume of the sample added to the sample retainer and the capacity of the sample retainer as volume of the sample injected to the sample separating column except that difference of the volume of the sample added to the sample retainer from the capacity of the sample retainer is within a predetermined range.

18. A liquid chromatograph, comprising a sample separating column, means for making an eluate to flow through the sample separating column, a sample retainer having a predetermined capacity, means for adding a sample to the sample retainer before injecting the added sample to the sample separating column to separate, means for detecting the sample separated by the sample separating column, wherein the sample injecting means has means for comparing volume of the sample added to the sample retainer with the capacity of the sample retainer.

* * * * *

UNITED STATES PATENT AND TRADEMARK OFFICE
CERTIFICATE OF CORRECTION

PATENT NO. : 5,512,170
DATED : April 30, 1996
INVENTOR(S) : Yoshiaki YAMADA et al.

It is certified that error appears in the above-identified patent and that said Letters Patent is hereby corrected as shown below:

| Column | Line | |
|---|---|---|
| 1 | 39 | After "know" change "of" to --the--. |
| 1 | 31 | Delete "over". |
| 1 | 37 | Change "no account of" to --failure to account for--. |
| 1 | 40 | Delete "the capacity of" (second occurrence). |
| 1 | 49 | Change "remained" to --retained--. |
| 3 | 52 | Delete "supporting for". |
| 4 | 37 | Change "come" to --go--. |
| 5 | 4 | Change "$A \geq B$" to --$A \leq B$--. |
| 5 | 21 | After "compares" delete "the". |

UNITED STATES PATENT AND TRADEMARK OFFICE
CERTIFICATE OF CORRECTION

PATENT NO. : 5,512,170
DATED : April 30, 1996
INVENTOR(S) : Yoshiaki YAMADA et al.

It is certified that error appears in the above-identified patent and that said Letters Patent is hereby corrected as shown below:

| Column | Line | |
|--------|------|---|
| 6 | 57 | Change "display" (first occurrence) to --displayed--. |
| 7 | 15 | Delete "over". |
| 8 | 15 | Delete "over". |

Signed and Sealed this

First Day of October, 1996

Attest:

BRUCE LEHMAN

Attesting Officer

Commissioner of Patents and Trademarks